United States Patent [19]
Bricot

[11] Patent Number: 5,158,526
[45] Date of Patent: Oct. 27, 1992

[54] METHOD AND PEDAL APPARATUS FOR SPINAL DISORDERS

[76] Inventor: Bernard Bricot, 3, rue des Flots-Bleus, 13007 Marseille, France

[21] Appl. No.: 549,642

[22] Filed: Jul. 9, 1990

Related U.S. Application Data

[63] Continuation of Ser. No. 346,801, May 3, 1989, abandoned, which is a continuation of Ser. No. 106,971, Sep. 28, 1987, abandoned, which is a continuation of Ser. No. 854,664, Apr. 18, 1986, abandoned, which is a continuation of Ser. No. 745,208, Jul. 17, 1985, abandoned, which is a continuation of Ser. No. 564,167, Dec. 29, 1983, abandoned, which is a continuation of Ser. No. 377,392, May 12, 1980, abandoned.

[30] Foreign Application Priority Data

May 13, 1981 [FR] France .................. 81 09663

[51] Int. Cl.$^5$ .......................... A61H 23/02
[52] U.S. Cl. ................................. 600/9
[58] Field of Search .................. 600/9, 12, 15

[56] References Cited

U.S. PATENT DOCUMENTS 3,848,581  11/1974  Miquel .

FOREIGN PATENT DOCUMENTS

| | | |
|---|---|---|
| 424257 | 5/1972 | Australia . |
| 690841 | 10/1970 | Belgium . |
| 2362908 | 6/1975 | Fed. Rep. of Germany ....... 128/1.3 |
| 1450093 | 11/1968 | France . |
| 2308384 | 11/1976 | France ........................ 128/1.3 |
| 2339410 | 9/1977 | France ........................ 128/1.3 |
| 2453654 | 11/1980 | France . |
| 2477022 | 9/1981 | France . |
| 894095 | 4/1968 | United Kingdom ............. 128/1.3 |
| 1648 | 5/1980 | World Int. Prop. O. .......... 128/1.3 |

OTHER PUBLICATIONS

Halliday et al., Physics, Part II, John Wiley & Sons, N.Y., 1967, pp. 919 and 1147.1153.
Mansfield et al., NMR Imaging in Biomedicine, Academic Press, N.Y., 1982, pp. 297–310.

Primary Examiner—Francis Jaworski
Attorney, Agent, or Firm—Sandler, Greenblum & Bernstein

[57] ABSTRACT

Method and apparatus for treating reflex zones of feet, by applying polarized undulatory energy flux generated by terrestrial fields or radiations to the reflex zones of feet.

25 Claims, 6 Drawing Sheets

METHOD AND PEDAL APPARATUS FOR SPINAL DISORDERS

This application is a continuation of application Ser. No. 07/346,801, filed May 3, 1989, which is a continuation of application Ser. No. 106,971 filed Sep. 28, 1987, which in turn is a continuation of U.S. Ser. No. 854,664 filed Apr. 18, 1986 which is a continuation of U.S. Ser. No. 745,208 filed Jul. 17, 1985, which is a continuation of U.S. Ser. No. 564,167 filed Dec. 29, 1983 which is a continuation of U.S. Ser. No. 377,392 filed May 12, 1982, all of which are now abandoned.

BACKGROUND OF THE INVENTION

1. Field of the Invention

The present invention relates to a therapeutic method and a pedal apparatus for treating the reflex zones of the feet, and, particularly for the treatment of troubles and ailments due to rachidian disturbance of equilibrium or misalignment of the spine.

2. Material Information Disclosure

Recent experiments have proven that the statural or skeletal muscular system, of which the rachidian muscles are a part, are under the influence of ascending proprioceptive chains whose point of departure is the foot or pedal. Since it is the point of normal support during erect standing:

vertebral alignment or equilibrium and statural or skeletal normality depend on the harmony of these different ascending proprioceptive chains statural normality;

all disturbance of the support on the ground has repercussions higher up by disharmony of stimulation of these chains. It is, therefore, apparent that one could remedy numerous troubles and ailments due to rachidian disequilibrium, by an action of re-equilibration or realignment of the ascending proprioceptive chains obtained by means of stimulation of the soles of the feet where the pedal points of departure of the chains are located. To that end, it has been proposed to correct the activation of the said chains with the help of therapeutic soles of particular form, but if these soles gave encouraging results in the treatment of certain ailments, they were affected by a number of inconveniences or insufficiencies. In effect:

they demand a very meticulous adjustment since the thickness of the wedges must be determined to one tenth of a millimeter;

their surveillance must be frequent, because in the course of the statural correction, thickness of the wedges must be modified;

they only act in strict bi-pedal support, that they only have a minimal effect in the treatment of individuals who practice a profession demanding the seated position;

also, the zones of stimulation are simple or double and only concern, therefore, one or two proprioceptive chains, and, therefore, other zones of stimulation would "modulate" the activation of the principal chains.

An aim of the present invention therefore is to remedy these insufficiencies by allowing for a recovery of equilibrium of the statural or skeletal muscular groups by reequilibration or realignment of the ascending proprioceptive chains, obtained by stimulation of the reflex zones of the foot and, more specifically, the reflex zones of the soles of the feet where the points of pedal departure of said chains are located, by means of a polarized undulatory flux of energy.

It has already been proposed (FR-A-2 453 654) to treat the human body by means of a continuous magnetic flux, pulsed or alternating produced by an electromagnet or by a permanent magnet and polarized by means of an apparatus for polarization of lights constituted, for example, by a polarized lens. Besides the fact that this therapeutic method, and the apparatus conceived for its use were not adapted for the stimulation of the reflex zones of the foot, they are not appropriate for such a treatment. In effect, experiments have proven that the application of a polarized magnetic flux produced by an electromagnet or by an ordinary unipolar permanent magnet on the reflex zones of the soles of the feet, very quickly caused the appearance of signs of magnetic intoxication with an aggravation of certain pains and the appearance of different pains. It has moreover been established that certain magnetic fields could be toxic for living organisms. One cannot therefore consider a permanent stimulation of the reflex zones, with the aid of the method and the above-mentioned apparatus, for the treatment of troubles of posture necessitating a permanent correction scoliosis, syphosis, etc.). Finally, far from favoring the re-equilibration of the ascending proprioceptive chains, one can conclude that the application of a polarized magnetic flux generated by an electromagnet or by an ordinary permanent magnet on the reflex zones of the foot, can aggravate the disequilibrium of the said chains, notably due to an intensity that is too strong.

SUMMARY OF THE INVENTION

The invention has for its object a therapeutic method and a pedal apparatus allowing for the application of a flux of polarized energy, such as a polarized magnetic flux of non-toxic intensity, on the reflex zones of the feet which leads to a reequilibration of the ascending proprioceptive chains, assuring a restoration of equilibrium of the statural or skeletal muscular groups, without the appearance of signs of magnetic intoxication during the process and at the end of treatment.

According to the therapeutic method of the invention, this result is obtained by inserting a polarizer between the reflex zones of the soles of the feet, and terrestrial fields or radiations, such as terrestrial magnetic field, making it possible to apply a polarized undulatory flux of energy, such as a polarized magnetic flux, generated by terrestrial fields of radiations on the said reflex zones.

The apparatus according to the invention is notable in the fact that it is constituted by a polarizer arranged in such a way as to constitute a pedal support apparatus, or incorporated with a pedal support apparatus, so as to make it possible to apply a polarized undulatory flux of energy generated by terrestrial fields or radiations, such as a polarized magnetic flux generated by the terrestrial magnetic field on the reflex zones of the soles of the feet. Besides the abovementioned advantages, the method and the apparatus for pedal application according to the invention have made it possible to provide, after several months of experimentation in the case of non-fixed lesions, the following effects (as described in terms recognized in the field of chiropractic medicine):

an instantaneous re-equilibration of the rachis, or realignment of the spine with disappearance of rachidian or spinal disorders;

a re-harmonization of the scapulary and lombar belts which equilibrate themselves in all planes;

a re-harmonization of rachidian curvatures;

a disappearance of all vertebral blockages;

a disappearance of minor intervertebral disturbances;

an opening of the holes of conjugation or alignment of vertebral foramen;

a disappearance of pains that may be caused by such disorders as referred to herein;

an increase in the vascularization in different areas, by liberation of nerve roots;

a disappearance of provoked pains and projected pains; and an improvement of the functional disturbances with respect to posture. Moreover, since the terrestrial fields or radiations such as the terrestrial magnetic fields are natural fields or radiations, their application to living organisms does not lead to the appearance of any sign of magnetic or any other intoxication.

BRIEF DESCRIPTION OF THE DRAWINGS

The attached drawings illustrate, by way of nonlimiting example, the interesting forms of example of the apparatus allowing for the application of an energy reticulated form on the underside of the feet, according to very advantageous embodiments of use of the therapeutic method according to the invention. In these drawings.

DESCRIPTION OF PREFERRED EMBODIMENTS OF THE INVENTION

The therapeutic method according to the invention is notable by the fact that one inserts a polarizer which provides for the application of a polarized undulatory flux of energy, such as a polarized magnetic flux, generated by terrestrial fields or radiations on the reflex zones, between the reflex zones of the sole of the foot or zones of stimulation of the points of pedal departure of the ascending proprioceptive chains, and the terrestrial fields or radiations such as the terrestrial magnetic field. In so doing it is possible to obtain a reequilibration of the said chains and, consequently, a re-equilibration of the statural or realignment of skeletal muscular groups influenced by said chains.

In a preferred manner, the polarized undulatory energy generated by the fields or terrestrial radiations, is applied on the underside of the feet by means of a pedal support apparatus such as soles, pattens, pedestal, etc.

The polarizer can be constituted by all anisotropic or polarizing substances known, such as polarizing or polaroid plates. In this case, the polarizer is, in a very desirable manner, constituted by two linear superimposed polarizing filters, whose axes of polarization are, in an advantageous fashion, intersecting at 90°. Such linear polarizing or polaroid filters are equally well known and frequently used in optics. They are easily constituted by flexible sheets of plastic materials containing microscopic crystals oriented when hot under electric fields, at the time of their manufacture, and act by dichroism. It is also possible to superimpose more than two polarizing or polaroid plates whose axes of polarization are, for example, intersected at 15°, 30°, 45°, 60°, 75°, etc., in such a way as to constitute polarizing filters of variable thickness allowing for one to obtain different characteristics of polarization. On the other hand, one can employ linear polarizing filters or circular polarizing filters. When the polarizer is constituted by two polarizing or polaroid plates whose axes intersect at 90°, the axes of polarization of the said polaroids preferably have an orientation of 45° with respect to the axis of the foot. Also, the axes of polarization of the polaroids may be intersected forming, among them different angles (for example, angles of 15°, 30°, 45°, 60°, 75°) and being able to have, with respect to the axis of the foot, an orientation differing from 45° (for example, angles of 30°-60°, or angles of 30°-45°-60°, angles of 15°-30°-45°-60°-75°). The polarizer can also be constituted by thickly laminated non-magnetic metal sheets or other thickly laminated substances having the same magnetic fluxes as the polaroid filters, by reason of their molecular or crystalline orientation. In case of the use of two, or more than two, superimposed sheets of metal or other thickly laminated material, the axes of orientation of these sheets, (direction of lamination) can be crossed in the manner indicated above for the polaroid filters.

Figure 1:
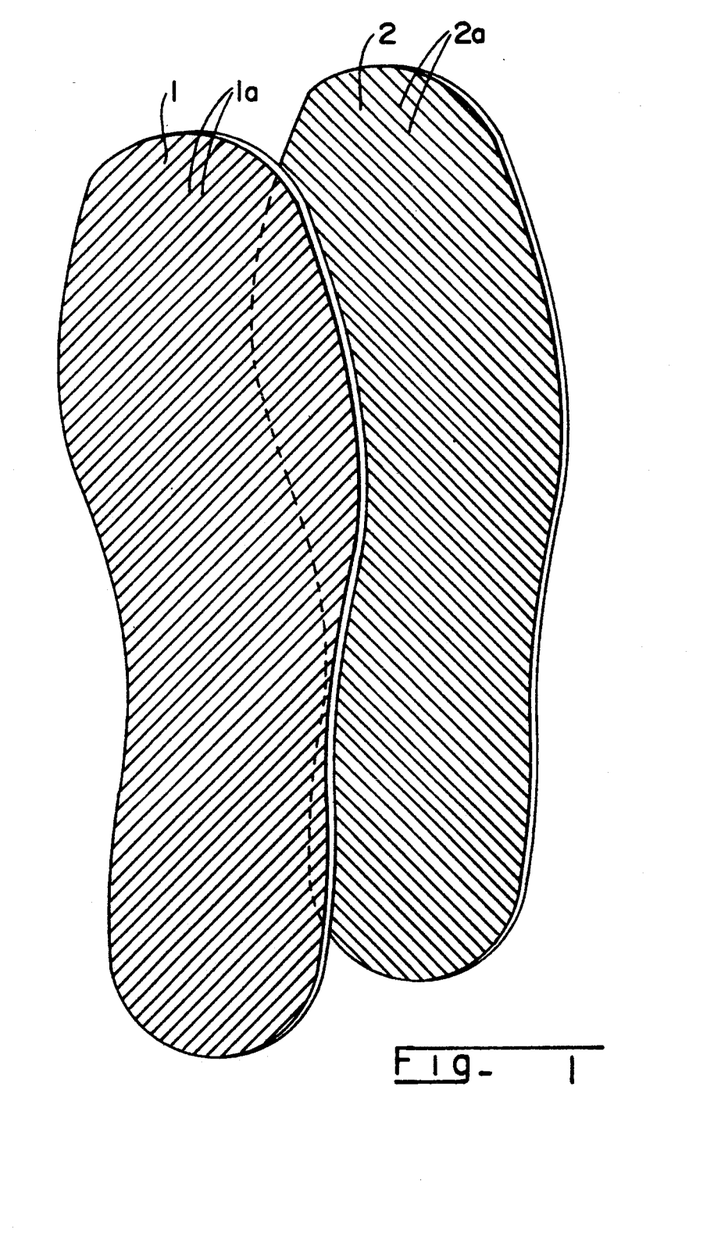
FIG. 1 is an exploded view in perspective of a medical sole allowing for the application of an energy reticulated form on the totality of the underside of the foot.
Figure 2:
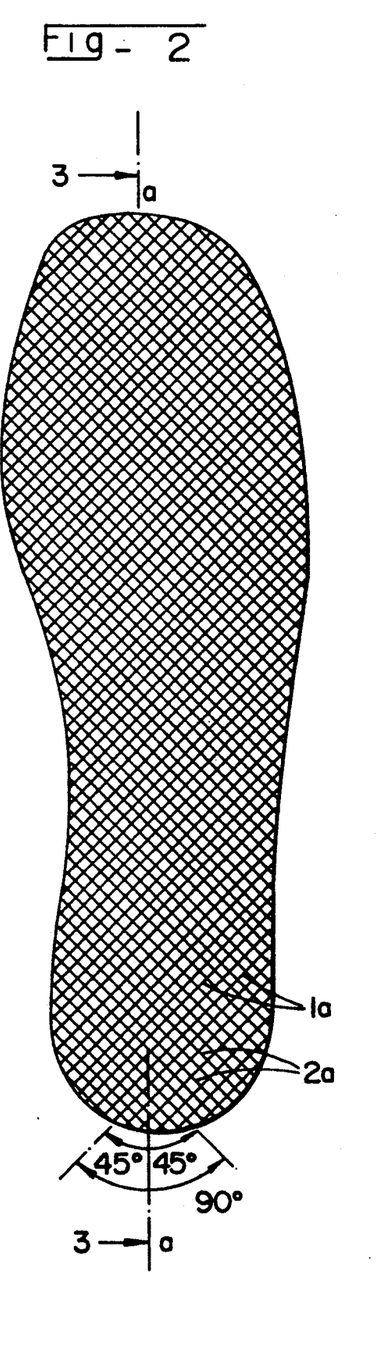
FIG. 2 is a planar view of this sole.
Figure 3:
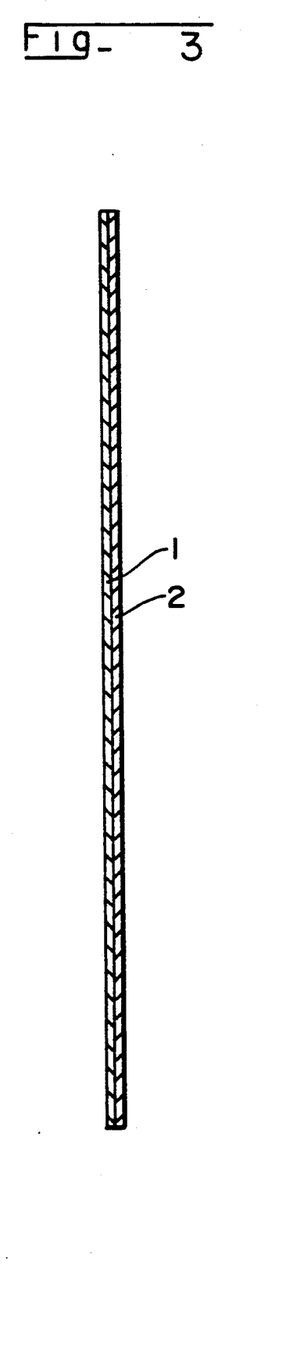
FIG. 3 is a cross-sectional view along line 3—3 of FIG. 2.

The polarizers constituted by flexible polarizing plates or polaroids, can be cut out in the form of the underside of the feet, to constitute a flexible patten or sole adapted to be lodged in a shoe, for example in case of treatment necessitating a long application of a polarized undulatory energy flux. Thus, as FIGS. 1-3 show, the polarizer is constituted by a patten or sole composed of two linear superimposed polarizing filters 1 and 2 whose axes of polarization, are schematized respectively, by the parallel lines 1a and by the parallel lines 2a which cross at 90°. On the other hand, according to this example, the axes of polarization 1a, 2a of the polaroids crossed at 90° have an orientation of 45° with respect to the longitudinal axis a-a of the sole (FIG. 2), that is to say with respect to the axis of the foot when the sole is placed under this latter.

Figure 4:
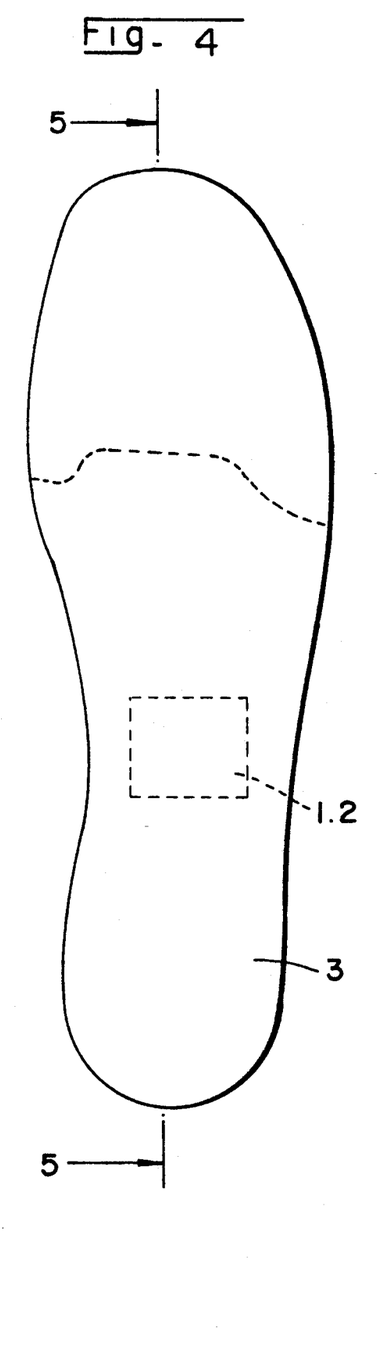
FIG. 4 is a planar view of a variation of the medical sole according to the invention.
Figure 5:
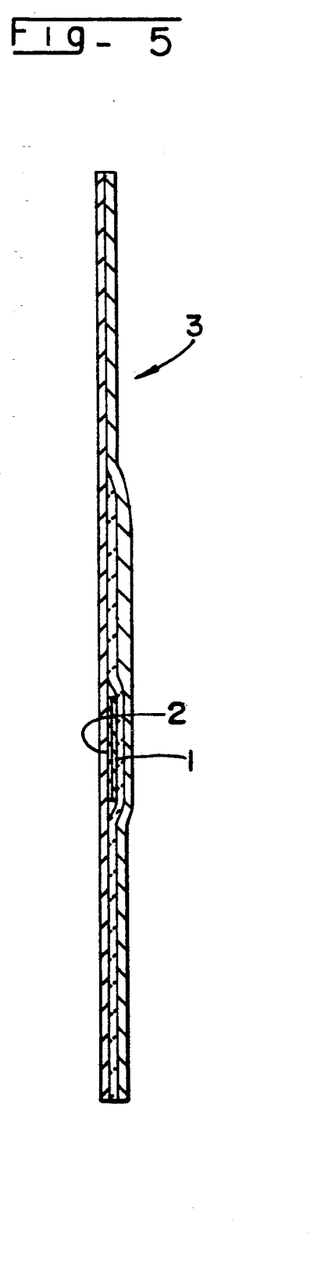
FIG. 5 is a longitudinal cross-sectional view along line 5—5 of FIG. 4.

It can be desirable to stimulate certain reflex zones only, of the sole of the foot. In this case, the polarizer apparatus has a reduced surface than that of the underside of the foot, and it is incorporated with a sole formed by means of traditional materials, at a location corresponding to the region where the reflex zone or zones to be treated are found. For example, taking into account the fact that the points of pedal departure of the principal ascending proprioceptive chains acting on the statural or skeletal muscular groups are found in the region of the arch, the polarizer apparatus can have a reduced dimension and be incorporated, according to any appropriate process, in the median zone of the patten or a sole, fabricated or executed in the known fashion of leather, skin, fabrics, felt, cork, or other materials, capable of being positioned in a shoe. FIGS. 4 and 5 show an embodiment of this type according to which the polarizer constituted by two superimposed polaroids 1, 2 is incorporated in the median portion of a patten or sole 3. Of course, it can also be placed at any other appropriate place in the sole or patten, according to the position of the reflex zone which it is necessary to stimulate.

Figures 6, 7:
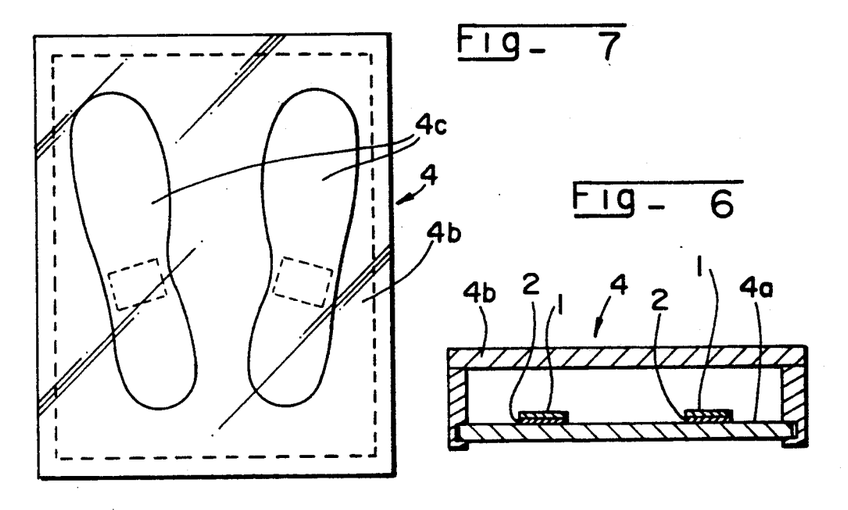
FIG. 6 is a transverse cross-sectional view of a pedestal allowing for the application of the therapeutic method according to the invention.
FIG. 7 is a planar view of this pedestal.
Figure 8:
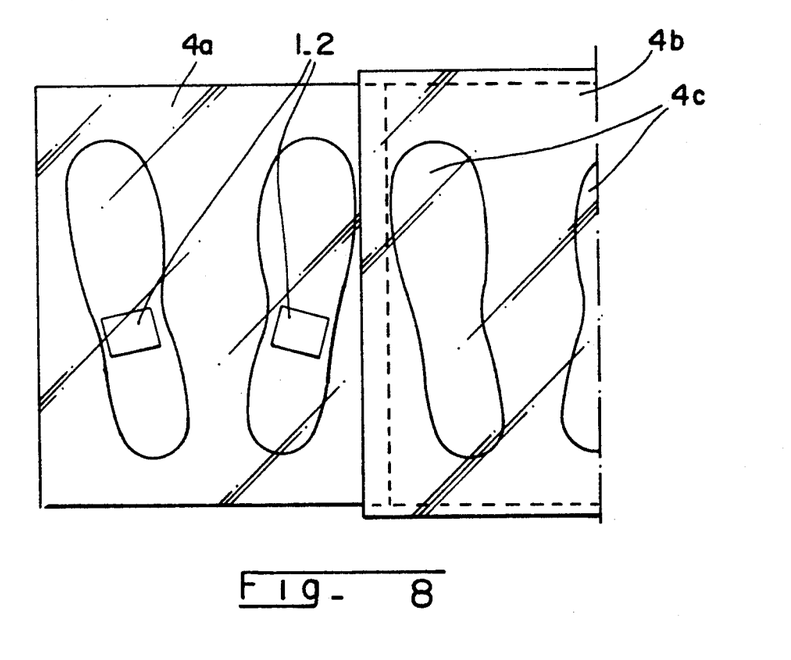
FIG. 8 is a planar view of the said pedestal with the end carrying the polarizers being represented in a partially recessed position.

According to another embodiment, one arranges two polarizers, having substantially the shape of the underside of the feet, or more reduced dimensions, on the upper plate or, preferably, on the base of a pedestal which can be arranged in front of the sink of a bathroom, in such a way that the user can stand there conveniently and regularly each time that he washes and dresses, that is to say without constraint and without loss of time, in the case where the treatment requires applications of polarized magnetic flux, or other polarized undulatory energy flux, of reduced duration. An embodiment of this type is shown in FIGS. 6-8. According to this embodiment, each of the two polarizers are constituted to have two superimposed polaroids 1, 2 which are installed on the base 4a of a pedestal 4, formed by a hollow casing whose base or upper plate 4b can be removable or journaled. On the upper side of the upper plate 4b, are positioned the imprints 4c or drawings of two feet, which are located above the polarizers supported by the base 4a. Therefore, when an individual is supported on pedestal 4 and positions his feet on the imprints or drawings 4c, the polarized undulatory energy flux generated by the terrestrial fields or radiations will be applied on the reflex zones of the foot to be treated.

Figure 9:
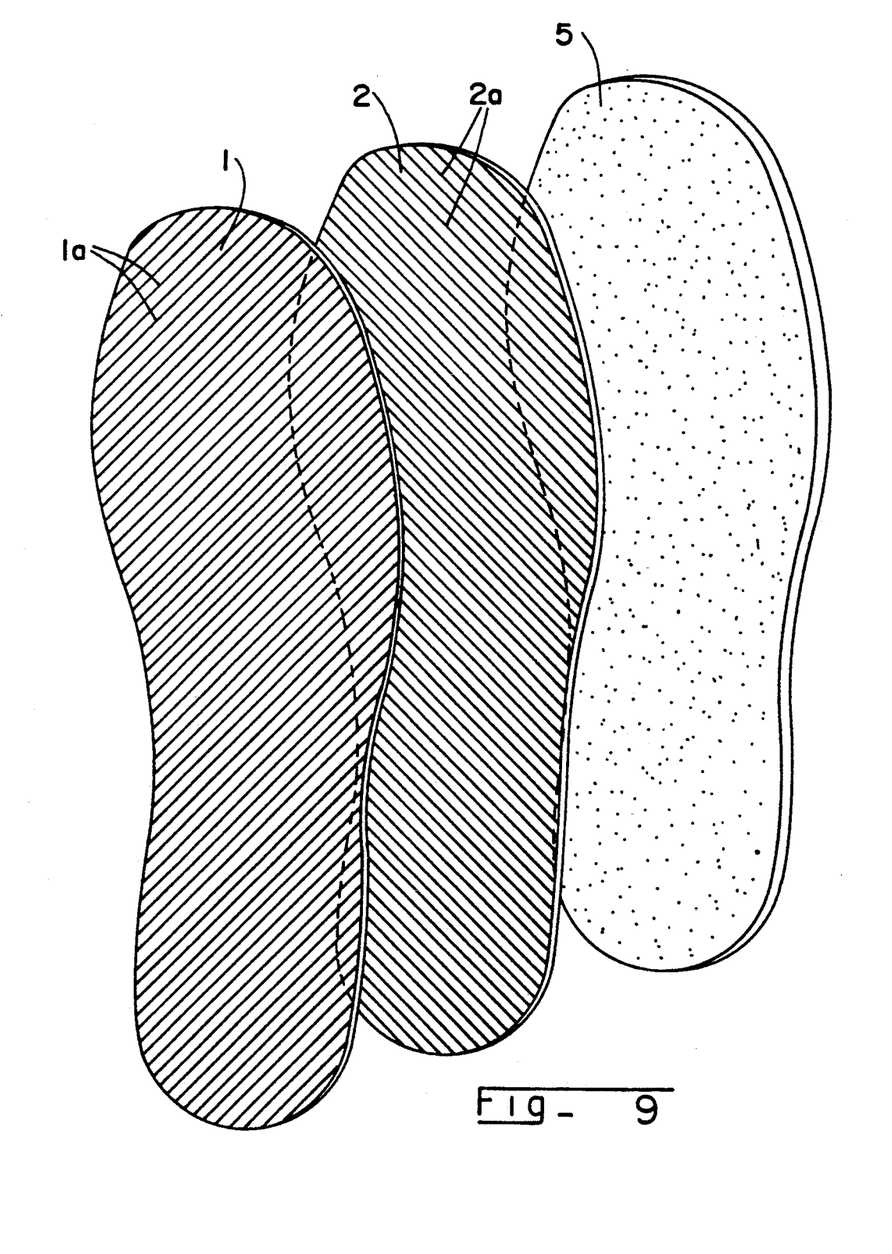
FIG. 9 is an exploded view in perspective of another mode of a medical sole providing for the application of a polarized magnetic energy on the totality of the underside of the foot.
Figure 10:
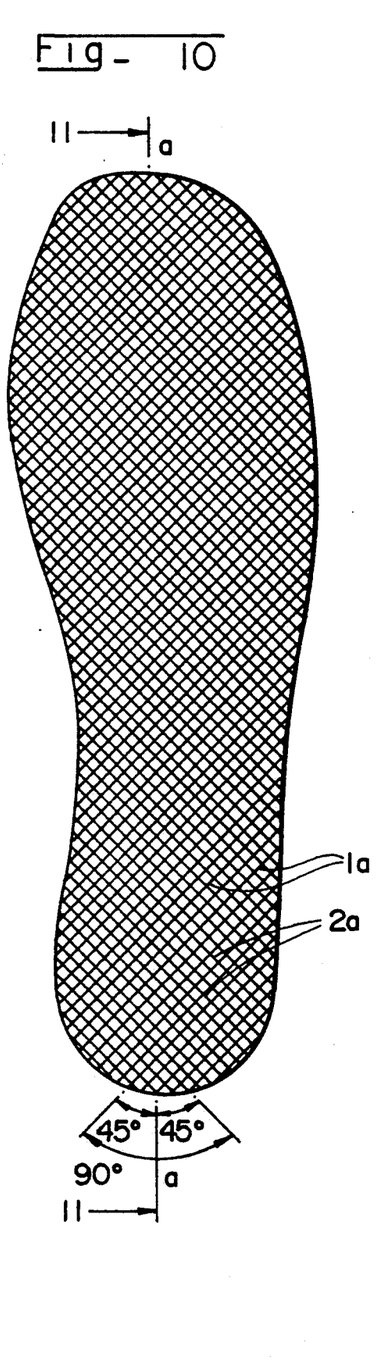
FIG. 10 is a planar view of this sole.
Figure 11:
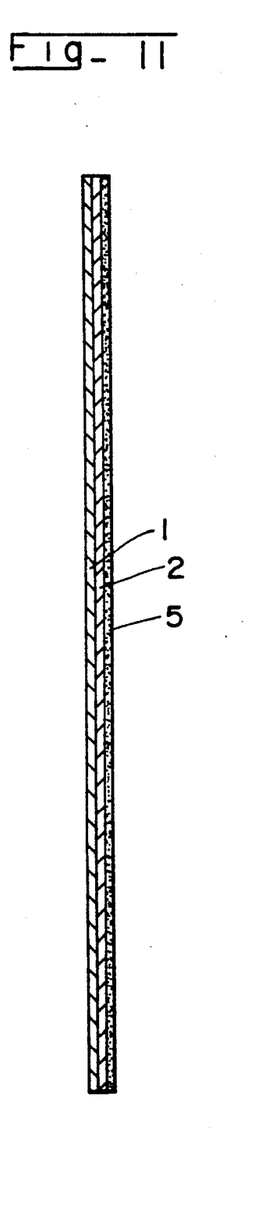
FIG. 11 is a cross-sectional view along line 11—11 of FIG. 10.

In the case of minimal functional pains, without substantial troubles of posture (minimal dorsalgia, lumbalgia, small muscular spasms, etc.) necessitating the application of a reinforced polarized magnetic flux during relatively short daily periods, an anisotropic and multipolar magnetic plate below the polarizer can be provided, this magnetic plate having the shapes and dimensions corresponding to that of said superimposed polarizer. The anisotropic magnetic plate is preferably constituted by a sheet of magnetized rubber of small thickness. Such flexible and anisotropic permanent magnets are well known. They are, for example, composed of magnetic ferrite powder and of a pliant elastomer, and they have a multipolar magnetization on one of their surfaces. One embodiment of this type is represented in FIGS. 9-11. According to this embodiment, the apparatus is constituted by a medical sole intended to cover the entire underside of the foot. This apparatus includes a multipolar and anisotropic magnetic sheet 5 having the shape of a sole and a polarizer a composed of two linear polarizing filters or polaroids 1, 2 of identical shape as that of said sheet positioned above the magnetized surface. The axes of polarization, respectively of 1a, and 2a, are intersected at 90° and have an orientation of 45° with respect to the longitudinal axis a-a of the said sole, and, consequently, with respect to the axis of the foot. In this case, the superimposed flexible sheets or plates 5, 1, 2, constituting the medical sole are assembled in any known manner. They can, for example, be housed in a neutral and flexible protecting envelope, or be united at their edge by means of any appropriate glue or peripheral coating. Of course, this apparatus of polarized magnetic flux can have reduced dimensions in such a way as to be able to be incorporated at any appropriate position of a patten or a sole executed in a classic fashion. It can also be installed on the upper plate or on the interior of the pedestal, as previously indicated.

I claim:

1. Apparatus for the treatment of reflex zones of feet comprising a pedal support and a polarizer incorporated with said pedal support.

2. Apparatus according to claim 1, wherein said polarizer is an anisotropic substance selected from the group consisting of linear and circular filters.

3. Apparatus according to claim 2, wherein said filters are flexible.

4. Apparatus according to claim 1, wherein said polarizer comprises at least two sheets of material having prescribed molecular or crystalline orientation, said sheets being superimposed in a manner so that the axes of said orientation ore crossed.

5. Apparatus according to claim 4, wherein said sheets are laminated.

6. Apparatus according to claim 4, wherein said material is a metal.

7. Apparatus according to claim 6, wherein said metal is non-magnetic.

8. Apparatus according to claim 1, wherein said polarizer comprises at least two superimposed polaroids.

9. Apparatus according to claim 8, wherein the axes of polarization of said polaroids intersect at 90°.

10. Apparatus according to claim 1, wherein said pedal support includes a sole corresponding in shape to the underside of feet.

11. Apparatus according to claim 10, wherein said polarizer comprises at least two superimposed polaroids.

12. Apparatus according to claim 11, wherein said polaroids are positioned in said sole at locations corresponding to the reflex zone regions of feet.

13. Apparatus according to claim 12, wherein said polaroids are positioned in the median zone of said sole.

14. Apparatus according to claim 11 wherein the axes of polarization of said polaroids form a preselected angle with respect to the longitudinal axis of said sole.

15. Apparatus according to claim 14, wherein said polaroids are superimposed in a manner whereby their axes of orientation form a 45° angle with respect to the longitudinal axis of said sole.

16. Apparatus according to claim 10, wherein said pedal support is a shoe.

17. A pedestal apparatus for the treatment of reflex zones of feet, comprising: an enclosure including an upper plate and a lower base, and polarizers located within said enclosure, said lower base supporting said polarizers, and said upper plate having means for indicating the location of said polarizers positioned vertically therebelow.

18. A therapeutic method for treating reflex zones of the feet comprising: placing a polarizer under the soles of feet.

19. A therapeutic method according to claim 18, further comprising associating said polarizer with a pedal support device prior to said placing step.

20. A therapeutic method according to claim 18, further comprising superimposing at least two intersecting polaroids to form said polarizer prior to said placing step.

21. A therapeutic method according to claim 20, wherein said polaroids are superposed so that the axes of polarization of said polaroids intersect at 90°.

22. A therapeutic method according to claim 20, wherein said polaroids are superimposed so that the axes of polarization form a preselected angle with respect to the longitudinal axis of said soles of the feet.

23. A therapeutic method according to claim 22 wherein said polaroids are superposed so that said axes of polarization have an orientation of 45° with respect to the longitudinal axis of the soles of the feet.

24. A therapeutic method according to claim 23, wherein a pair of superimposed polaroids are superimposed to form said polarizer.

25. A therapeutic method according to claim 18, further comprising superimposing at least two sheets of material of prescribed molecular or crystalline orientation whose axes of orientation are crossed to form said polarizer prior to said placing step.

* * * * *